United States Patent
Ittel et al.

(10) Patent No.: US 6,232,259 B1
(45) Date of Patent: May 15, 2001

(54) PREPARATION OF TRANSITION METAL IMINE COMPLEXES

(75) Inventors: Steven Dale Ittel; Samuel David Arthur; Joel David Citron, all of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/277,910

(22) Filed: Mar. 29, 1999

Related U.S. Application Data

(60) Provisional application No. 60/080,051, filed on Mar. 31, 1998.

(51) Int. Cl.$^7$ .............................. B01J 31/00; B01J 31/18; B01J 31/12
(52) U.S. Cl. ................... 502/155; 502/150; 502/151; 502/152; 502/162; 502/167; 502/172
(58) Field of Search ..................................... 502/150, 151, 502/152, 155, 162, 167, 172

(56) References Cited

U.S. PATENT DOCUMENTS

| | | | |
|---|---|---|---|
| 5,714,556 | 2/1998 | Johnson et al. | 526/135 |
| 5,942,461 | * 8/1999 | Brown et al. | 502/154 |
| 5,955,555 | * 8/1999 | Bennett | 526/133 |

FOREIGN PATENT DOCUMENTS

| | | |
|---|---|---|
| WO 96/23010 | 8/1996 | (WO). |
| WO 97/38024 | 10/1997 | (WO). |
| WO 97/48735 | 12/1997 | (WO). |
| WO 97/48737 | 12/1997 | (WO). |

OTHER PUBLICATIONS

Heindirk tom Dieck, et al., Diazadiene complexes of Group 4 metals I. Synthesis of mono–, bis– and tris(diazadiene) titanium complexes and the structure of diazadienedichlorotitanium, *Inorganica Chimica Acta*, 177, 191–197, 1990, No Month Available.

Rob van Asselt, et al., Insertion of Carbon Monoxide and Alkenes in Palladium–Carbon Bonds of Complexes Containing Rigid Bidentat Nitrogen Ligands: The First Example of Isolated Complexes in Stepwise Successive Insertion Reactions on the Way to Polyketones, *J. Am. Chem. Soc.*, 116, 977–985, 1994. No Month Available.

Heindirk tom Dieck, et al., Diazadien Nickel Complexes, Bromo–diazadien–Nickel(I), *Z. Naturforsch,* 33 b, 1381–1385, 1978 No Month Available.

Hans Georg von Schnering, et al., Crystal and Molecular Structure of Bromo–(3,8–diisopropyl–2, 9–dimethyl–4.7–diaza–4,6–decadienyl–N,N') nickel (II), a Square Planar Complex with a Tridentate N,N,C–Chelate, *Chem. Ber.,* 109, 1665–1669, 1976, No Month Available.

Heindirk tom Dieck, et al., Metalation of a Non–activated Alkyl Group in Nickel Complexes, *Chem. Ber.,* 109, 1657–1664, 1976, No Month Available.

Rob van Asselt, et al., Synthesis and characterization of rigid bidentate nitrogen ligands and some examples of coordination to divalent palladium. X–ray crystal structures of bis(p-–tolylimino)acenaphthene and methylchloro[bis(o, o'–diisopropylphenyl–imino) acenaphthene] palladium (II), *Recl. Trav. Chim. Pays–Bas,* 113, 88–98, 1994, No Month Available.

PCT/US 99/06818 PCT International Search Report dated Jul. 30, 1999.

* cited by examiner

*Primary Examiner*—Elizabeth D. Wood

(57) ABSTRACT

Transition metal imine complexes can be prepared by reacting the imine precursors, a carbonyl compound and a primary amine, in the presence of a selected transition metal compound. The complexes may be used as catalysts for olefin polymerization.

17 Claims, No Drawings

PREPARATION OF TRANSITION METAL IMINE COMPLEXES

This application claims the benefit of U.S. Provisional Application Ser. No. 60/080,051 filed Mar. 31, 1998.

FIELD OF THE INVENTION

Preparation of imine complexes of certain transition metals from selected metal compounds and organic compounds which are precursors of imines in essentially a single step are described. The imine complexes are useful in the polymerization of olefins, and may be used directly without isolation.

TECHNICAL BACKGROUND

Imine complexes of certain transition metals such as iron, palladium, cobalt, nickel and others are important parts of catalyst systems for the polymerization of olefins, see for instance U.S. Pat. No. 5,714,556, World Patent Applications 96/23010, 97/48737, 97/48735, 97/38024, and U.S. patent application 08/991372, filed Dec. 16, 1997 (now U.S. Pat. No. 955,555) all of which are hereby included by reference. These and other references generally describe the synthesis of these types of imine complexes as the reaction of the imine containing ligand with various types of transition metal compounds to form the transition metal imine complex. These methods usually involve the use of substantially anhydrous conditions to avoid hydrolysis of the starting transition metal compound and/or any intermediates or the desired final complex.

For the most part, the imines themselves are not commercially available, usually being made from the corresponding carbonyl compound, such as a ketone or aldehyde, and an amine, often an aromatic amine. When made by this method, water is a byproduct. Since this imine forming reaction is usually considered to be an equilibrium, to drive the reaction to completion the water is often removed during the synthesis of the imine, for example by distillation, preferably azeotropic distillation, or by formation of a hydrate, preferably an inorganic hydrate.

Thus imine complexes of transition metals are often made in two step processes, imine synthesis, and then synthesis of the metal complex. A simpler, especially one step, synthesis would be preferable if they used the same starting materials since they would usually be cheaper than a two step synthesis.

Many complexes of imines and transition metals have been synthesized and reported in the literature. In addition to the above references, see for instance: H. tom Dieck et al., Inorg. Chim. Acta, vol. 177, p. 191–197 (1990); R. van Asselt, et al., J. Am. Chem. Soc., vol. 116, p. 977–985 (1994); H. tom Dieck, et al., Z. Naturforsch. B, vol. 33, p. 1381 et seq. (1978); H. G. von Schnering, et al., Chem. Ber., vol. 109, p. 1665 et seq. (1976); and H. tom Dieck et al., Chem. Ber., vol. 109, p. 1657 et seq. (1976).

R. van Asselt, et al., Recl. Trav. Chim. Pays-Bas., vol. 113, p. 88–98 (1994) describes the synthesis of certain zinc and nickel α-diimine complexes from the diketone and aromatic amine. In many of the syntheses, (glacial) acetic acid is present.

SUMMARY OF THE INVENTION

This invention concerns a process for the production of a transition metal complex of an imine, comprising, contacting under imine forming conditions in an aprotic solvent, a transition metal compound, a first organic compound containing at least one aldehyde or ketone group, and a second organic compound which is a primary amine to form said transition metal complex of said imine, and provided that said transition metal is nickel, palladium, iron and cobalt.

DETAILS OF THE INVENTION

It is well known that imines can be made by the reaction of a carbonyl group such as a ketone or aldehyde with a primary amine, the reaction being:

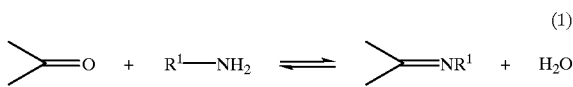

(1)

Since (1) is generally thought of as being an equilibrium reaction, it is usually driven to completion (formation of the imine) by removing the byproduct water that is formed. This can be done in a variety of ways, for instance removing the water by azeotropic distillation or as a hydrate of an inorganic salt. In order to efficiently utilize carbonyl compound and amine used in (1), they should preferably be present in the reaction in approximately the same ratio as they are in the product.

It has suprisingly been found that imine complexes [the imine(s) in the complex may contain one or more imine groups] of certain transition metals can be made in an aprotic solvent by addition of salts of those metals to a process in which reaction (1) is being carried out, even though water is generated as a byproduct. Thus reaction (1) is carried out in the presence of a suitable salt of the desired transition metal. The ratio of transition metal salt to the other ingredients is not critical, but in order to efficiently utilize all of the ingredients the ratio of moles transition metal compound to moles of the other reactants is such that they are approximately the same as they are in final desired imine complex. The transition metal compound is preferably present at the beginning of the process, but may be added at any time during the formation of the imine.

Useful transition metal compounds include metal halides, especially chlorides and bromides, and carboxylates. Zerovalent metal compounds that are not too sensitive to water may be used in conjunction with a suitable oxidizing agent (which are known in the art). Preferred transition metal compounds are halides, especially chlorides and bromides.

Any transition metal may be used. Transition metals are those metals in Groups 3–12 (IUPAC notation), and metals in Groups 3–11 are preferred and metals in Groups 8–10 are especially preferred. Specific preferred transition metals are nickel, cobalt, iron and palladium, and nickel is especially preferred.

Process conditions for forming imines are well known and will be found in the various references cited in the Technical Background section, and also in R. L. Reeves in S. Patai, Ed., The Chemistry of the Carbonyl Group, Interscience Publishers, London, 1966, p. 608–619, and J. K. Whitesell in B. M. Trost, et al., Ed., Comprehensive Organic Synthesis, Vol. 6, Pergamon Press, Oxford, 1991, p. 719, which are both hereby included by reference.

The present process is preferably performed at a temperature of about 0° C. to about 250° C., more preferably about 20° C. to about 130° C. While pressure is not critical, and the process will probably be most often be carried out at ambient pressure, higher or lower pressures (than atmospheric pressure) may be used, for example to control the process temperature while distilling off byproduct water.

Preferred primary amines in the process are aryl amines, i.e., $R^1$ is an aryl or substituted aryl group. Aryl herein includes groups that have one or more aromatic rings which may be fused, as in naphthyl, or connected by a covalent bond, as in 2-phenylphenyl (o-biphenylyl). It is preferred that the aromatic rings of the aryl group are carbocyclic rings, and it is more preferred that $R^1$ is phenyl or substituted phenyl. Useful substitutents on a substituted phenyl group are alkyl, especially alkyl containing 1 to 4 carbon atoms, halo, especially chloro, phenyl, and halo substituted alkyl, especially fluoro substituted alkyl. It is also preferred that the phenyl group be substituted in the 2, or 2 and 6, positions.

The reaction is conducted in an aprotic solvent. By aprotic is meant the solvent has no protons whose pKa is about 20 or more, more preferably about 25 or more. Useful solvents include aromatic hydrocarbons such as benzene and toluene, xylene, chlorobenzene and o-dichlorobenzene. Since the transition metal complex may often be used in conjunction with other types of compounds (such as alkyl aluminum compounds) as a catalyst system for the polymerization of olefin, the absence of protic solvents is an advantage, since the solvent need not be removed before adding an alkyl aluminum compound.

The carbonyl compound may contain more than one carbonyl group which may form an imine. Useful carbonyl compounds include α,β-diones, 2,6-pyridinedicarboxyaldehydes, 2,6-diacylpyridines, cyclic α,β-diones, 1,3-diones and ketoaldehydes. Specific useful carbonyl compounds include glyoxal, 2,3-butanedione, acenapthenequinone, 2,6-diacetylpyridine, 2,6-pyridinedicarboxaldehyde, 1,2-cyclohexanedione, and pyruvaldehyde.

The transition metal imine complex, after it is made, may be isolated, as by removing the solvent under vacuum or by crystallization, or the solution may be used directly (i.e., without isolation of the complex, but the solution may be filtered to remove any insoluble impurities) in a polymerization of one or more olefins. Olefins which may be polymerized with various transition metal complexes of imines, and the conditions for polymerizations will be found in U.S. Pat. No. 5,714,556, World Patent Applications 96/23010, 97/48737, 97/48735, 97/38024, and U.S. patent application Ser. No. 08/991372, filed Dec. 16, 1997, (now U.S. Pat. No. 955,555) and other references.

In the Examples, all pressures are gauge pressures.

EXAMPLE 1

(I)

Nickel dibromide was purified of insoluble material by dissolving 2.22 g anhydrous nickel dibromide in 100 mL ethanol containing 1 mL water, filtering through diatomaceous earth and rotary evaporating dry. A mixture of 1.84 g (10.1 mmol) acenapthenequinone, 3.00 g (20.0 mmol) 2,6-diethylaniline, 2.1 g (9.6 mmol) nickel dibromide and 50 mL toluene was refluxed under nitrogen with water removal for 24 h to give a deep red-black reaction mixture. The mixture was rotary evaporated to remove toluene and the concentrate was stirred with 50 mL methylene chloride and filtered through diatomaceous earth to remove unreacted nickel bromide. The filtrate was rotary evaporated and then held under high vacuum to yield 4.84 g dark red, waxy solids. The product was crushed and slurried in 40 mL hexane and suction-filtered. Drying under nitrogen yielded 3.95 g (I) as a brown, methylene chloride-soluble powder.

EXAMPLE 2

A suspension of 2.0 mg (0.0030 mmol) (I) of Example 1 in 5 mL dry, deaerated toluene was mixed with 1.0 mL 1.7M modified methylaluminoxane in toluene (contains about 30% isobutyl groups) in a septum vial under nitrogen, swirling occasionally over 5 min, resulting in a dark maroon solution. A 600-mL stirred autoclave was loaded with 200 mL dry toluene. The solvent was stirred and saturated with ethylene at 50° C. and 0.7 MPa for 10 min. The autoclave was vented and the toluene solution of catalyst was taken up into a 10-mL syringe and was injected into the autoclave through a head port. The autoclave was immediately pressured to 1.0 MPa with ethylene and was stirred for 30 min in a 50° C. water bath as ethylene was fed to maintain pressure. After 30 min the ethylene was vented and resulting clear polymer gel was extracted with acetone and vacuum-oven dried (70° C/nitrogen purge) to yield 6.7 g polyethylene.

EXAMPLE 3

(II)

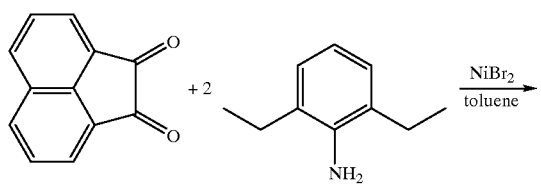

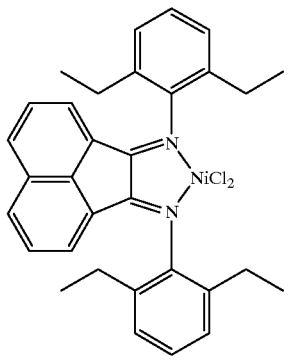

A mixture of 1.84 g (10.1 mmol) acenaphthenequinone, 3.00 g (20.0 mmol) 2,6-diethylaniline, 2.25g (9.5 mmol) nickel dichloride hexahydrate, 30 mg p-toluenesulfonic acid and 50 mL toluene was refluxed for 48 h under nitrogen with water removal. The deep red-brown reaction mixture was suction-filtered on a glass fritted funnel to remove unreacted nickel dichloride. The black filtrate solution was sparged with nitrogen before using as a catalyst.

EXAMPLE 4

A mixture of 20 mL dry, deaerated toluene and 1.0 mL 1.7M modified methylalumoxane was magnetically stirred at room temperature under 41 kPa ethylene in a 50-mL Schlenk flask for a few minutes to saturate the solvent with ethylene. Then 1.5 mL of the solution of (II) made in Example 10 was added; a black solution immediately resulted. This solution was stirred under 41 kPa ethylene for 16 h; it remained black but became more viscous with time. The ethylene was vented and the solution was stirred with 25 mL 6N HCl and 20 mL additional toluene, and the toluene layer was separated, water-washed and rotary-evaporated to yield, after washing with methylene chloride and acetone and vacuum-oven drying (70° C.), 0.96 g of soft, tacky polyethylene.

What is claimed is:

1. A process for the production of a transition metal complex of an imine of a first organic compound containing at least one aldehyde or ketone group, and a second organic compound which is a primary amine, comprising the step of contacting a transition metal compound with said first organic compound and said second organic compound under imine forming conditions in an aprotic solvent to form said transition metal complex, and provided that the transition metal of said transition metal compound is nickel, palladium, iron or cobalt.

2. The process as recited in claim 1 wherein byproduct water is removed by distillation or formation of a hydrate.

3. The process as recited in claim 1 wherein water is removed by azeotropic distillation.

4. The process as recited in claim 1 or 3 wherein said second compound is a primary aryl amine or a substituted aryl primary amine.

5. The process as recited in claim 1 or 3 wherein said transition metal is nickel.

6. The process as recited in claim 1 or 3 wherein said transition metal compound is a chloride, bromide, or carboxylate.

7. The process as recited in claim 1 wherein a temperature is about 0° C. to about 250° C.

8. The process as recited in claim 1 wherein said aprotic solvent is a hydrocarbon.

9. The process as recited in claim 5 wherein said second compound is a primary amine or a substituted aryl primary amine.

10. The process as recited in claim 1 wherein said second compound is a primary amine or a substituted aryl primary amine.

11. The process as recited in claim 6 wherein transition metal is nickel.

12. The process as recited in claim 1, wherein the transition metal compound is a transition metal salt.

13. The process as recited in claim 1, wherein the transition metal salt is a transition metal halide.

14. The process as recited in claim 1 wherein said first organic compound is a 2,6-pyridinecarboxaldehyde or a 2,6-diacylpyridine.

15. The process as recited in claim 14, wherein said transition metal compound is an iron compound.

16. The process as recited in claim 14, wherein the transition metal compound is an iron salt.

17. The process as recited in claim 14, wherein the transition metal salt is an iron halide.

* * * * *